(12) United States Patent
Mashita

(10) Patent No.: US 9,395,314 B2
(45) Date of Patent: Jul. 19, 2016

(54) METHOD OF EVALUATING NEUTRON SCATTERING LENGTH DENSITY

(71) Applicant: SUMITOMO RUBBER INDUSTRIES, LTD., Kobe-shi, Hyogo (JP)

(72) Inventor: Ryo Mashita, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 32 days.

(21) Appl. No.: 14/268,454

(22) Filed: May 2, 2014

(65) Prior Publication Data

US 2014/0341354 A1    Nov. 20, 2014

(30) Foreign Application Priority Data

May 17, 2013    (JP) ................... 2013-105436

(51) Int. Cl.
  *G01N 23/20*  (2006.01)
  *G01N 23/202*  (2006.01)
  *G01N 23/201*  (2006.01)
(52) U.S. Cl.
  CPC ............ *G01N 23/202* (2013.01); *G01N 23/201* (2013.01)
(58) Field of Classification Search
  CPC .................................................. G01N 21/202
  See application file for complete search history.

(56) References Cited

FOREIGN PATENT DOCUMENTS

JP    2013-30286 A    2/2013

OTHER PUBLICATIONS

Thomas Zemb and Olivier Diat, "What can we learn from combined SAXS and SANS measurements of the same sample containing surfactants?" Journal of Physics: Conference Series 247 (2010) 012002, 14 pages. <doi:10.1088/1742-6596/247/1/012002>.*
Yamauchi et al. "Structural Study of Natural Rubber Thermoplastic Elastomers and Their Composites with Carbon Black by Small-Angle Neutron Scattering and Transmission Electron Microscopy", Composites: Part A 36(2005), p. 423-429.*
Yamauchi et al., "Structural Study of Natural Rubber Thermoplastic Elastomers and their Composites with Carbon Black by Small-Angle Neutron Scattering and Transmission Electron Microscopy", Composites: Part A, vol. 36, No. 4, 2005, pp. 423-429.

* cited by examiner

*Primary Examiner* — Casey Bryant
(74) *Attorney, Agent, or Firm* — Birch, Stewart, Kolasch & Birch, LLP

(57) ABSTRACT

A method of evaluating the neutron scattering length density, capable of accurately determining the neutron scattering length density is provided. The method evaluates the neutron scattering length density of scatterers in a material, including determining the neutron scattering length density based on a scattering intensity curve obtained by neutron scattering measurement, with use of a scattering intensity curve obtained by X-ray scattering measurement.

4 Claims, 3 Drawing Sheets

METHOD OF EVALUATING NEUTRON SCATTERING LENGTH DENSITY

TECHNICAL FIELD

The present invention relates to a method of evaluating the neutron scattering length density.

BACKGROUND ART

In the evaluation of the molecular structure of a material by neutron scattering/diffraction measurement, the structural information can be calculated based on the neutron scattering length density of the target material. Here, in the case of scattering of the incident (neutron) wave from a single spinless atomic nucleus, the neutron scattering length indicates the degree of neutron scattering from this atomic nucleus, and is calculated by dividing the scattering length by the density of the target material.

Thus, the neutron scattering length density of single-composition target materials can be simply determined depending on the kind, the number and the density of the atoms in the target. On the other hand, in the case of non-single-composition target materials, for example, a target material that is a mixture of multiple components, with their ratio not determined, it is difficult to accurately determine the neutron scattering length density of the target materials.

SUMMARY OF INVENTION

Technical Problem

The present invention aims to provide a method of evaluating the neutron scattering length density which can solve the above problem and can accurately determine the neutron scattering length density.

Solution to Problem

The present invention relates to a method of evaluating a neutron scattering length density of scatterers in a material, including determining the neutron scattering length density based on a scattering intensity curve obtained by neutron scattering measurement, with use of a scattering intensity curve obtained by X-ray scattering measurement.

Preferably, the X-ray scattering measurement is small-angle X-ray scattering measurement and the neutron scattering measurement is small-angle neutron scattering measurement.

The material preferably includes one or more diene polymers.

The small-angle neutron scattering measurement is preferably contrast variation small-angle neutron scattering measurement in which a deuteration level of a swelling solvent or a deuteration level of the material is varied.

The evaluation method is preferably that in which the neutron scattering length density is determined by calculation such that the shape of the scattering intensity curve of the scatterers in the material obtained by the small-angle X-ray scattering measurement matches the shape of a scattering intensity curve of only the scatterers detected by the small-angle X-ray scattering measurement, separated from the scattering intensity curves obtained by the contrast variation small-angle neutron scattering measurement.

Advantageous Effects of Invention

The present invention provides a method of evaluating the neutron scattering length density of scatterers in a material, including determining the neutron scattering length density based on a scattering intensity curve obtained by neutron scattering measurement, with use of a scattering intensity curve obtained by X-ray scattering measurement. This makes it possible to accurately determine the neutron scattering length density. Further, such accurate determination of the neutron scattering length density of scatterers leads to accurate determination of the molecular structure (e.g. radius of gyration, the number per unit volume) of scatterers. In addition, since the molecular structure of scatterers correlates to the material properties (e.g. energy loss, abrasion resistance), the method also allows more accurate evaluation of the material properties.

Even in the case where the material to be evaluated contains multiple components and the scatterers contained in the material are a mixture of multiple compositions, the present invention also enables the determination of the mixing ratio of these compositions.

DESCRIPTION OF EMBODIMENTS

Figure 1:
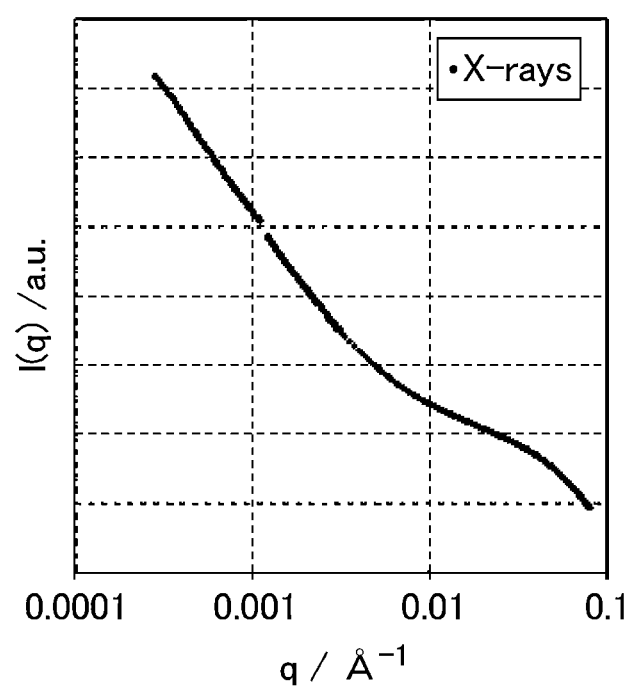
FIG. 1 shows an example of a scattering intensity curve of an EXAMPLE sample obtained by small-angle X-ray scattering measurement.

The present invention relates to a method of evaluating the neutron scattering length density of scatters in a material, including determining the neutron scattering length density based on a scattering intensity curve obtained by neutron scattering measurement, with use of a scattering intensity curve obtained by X-ray scattering measurement.

In the present invention, the neutron scattering length density can be accurately determined by, for example, varying the neutron scattering length density of scatterers in a material such that the shape of a scattering intensity curve of the scatterers in the material obtained by small-angle X-ray scattering measurement or the like matches the shape of a scattering intensity curve of the scatterers in the material which is obtained by separating the scattering intensity curve of only the scatterers detected by the small-angle X-ray scattering measurement or the like from the measurement results of contrast variation small-angle neutron scattering measurement or the like. Thus, the neutron scattering length density can be determined based on a scattering intensity curve preliminarily determined by neutron scattering measurement, with reference to a scattering intensity curve preliminarily determined by X-ray scattering measurement.

In the present invention, X-ray scattering measurement is performed to give a scattering intensity curve. The X-ray scattering measurement may suitably be small-angle X-ray scattering (SAXS) measurement (scattering angle: typically 10 degrees or smaller) wherein a material (sample) such as a polymer material is irradiated with X-rays to measure the scattering intensity. In the small-angle X-ray scattering, the structural information of a substance can be obtained by measuring the X-rays scattered at small scattering angles among the scattered X-rays resulting from the irradiation of the substance with X-rays. In this way, ordered structures on the order of a few nanometers (e.g., microphase-separated structures) of polymer materials can be analyzed.

In order to obtain molecular structure information with high accuracy, the SAXS measurement should desirably measures an X-ray scattering profile with a high S/N ratio. Thus, the X-rays radiated from a synchrotron preferably have a brilliance of at least $10^{10}$ (photons/s/mrad$^2$/mm$^2$/0.1% bw). The symbol bw represents the band width of X-rays radiated from a synchrotron. Examples of such synchrotrons include the beamlines BL03XU and BL20XU of the large synchrotron radiation facility "SPring-8" belonging to Japan Synchrotron Radiation Research Institute.

The brilliance (photons/s/mrad$^2$/mm$^2$/0.1% bw) of the X-rays is preferably $10^{10}$ or higher, and more preferably $10^{12}$ or higher. The upper limit thereof is not particularly limited, and the X-ray intensity used is preferably low enough not to cause radiation damage.

The number of photons (photons/s) in the X-rays is preferably $10^7$ or more, and more preferably $10^9$ or more. The upper limit of the number of photons is not particularly limited, and the X-ray intensity used is preferably low enough not to cause radiation damage.

In the present invention, neutron scattering measurement is performed to give a scattering intensity curve. The neutron scattering measurement may suitably be small-angle neutron scattering (SANS) measurement (scattering angle: typically 10 degrees or smaller) wherein a polymer material is irradiated with neutrons to measure the scattering intensity. In the small-angle neutron scattering, the structural information of a substance can be obtained by measuring the neutrons scattered at small scattering angles among the scattered neutrons resulting from the irradiation of the substance with neutrons. In this way, ordered structures on the order of a few nanometers (e.g., microphase-separated structures) of polymer materials can be analyzed.

The SANS measurement may utilize a known magnetic structure-based technique or deuteration technique. In the case of using a deuteration technique, for example, a material such as a polymer material is made to swell in a deuterated solvent, and the material in equilibrium in the deuterated solvent is irradiated with neutrons to measure the scattering intensity. Examples of the deuterated solvents (swelling solvents) for swelling materials include heavy water, deuterated hexane, deuterated toluene, deuterated chloroform, deuterated methanol, deuterated DMSO (($D_3C$)$_2$S=O), deuterated tetrahydrofuran, deuterated acetonitrile, deuterated dichloromethane, deuterated benzene, and deuterated N,N-dimethylformamide.

The SANS measurement may suitably be contrast variation small-angle neutron scattering measurement while varying the deuteration level of the swelling solvent or contrast variation small-angle neutron scattering measurement while varying the deuteration level of the material. Such a measurement allows accurate determination of the neutron scattering length density by calculation such that the shape of a scattering intensity curve obtained by small-angle X-ray scattering measurement matches the shape of a scattering intensity curve of only the scatterers detected by the small-angle X-ray scattering measurement, separated from scattering intensity curves obtained by contrast variation small-angle neutron scattering measurement.

The neutrons to be used in the neutron scattering measurement such as SANS can be obtained from, for example, the SANS-J beamline at the JRR-3 research reactor belonging to Japan Atomic Energy Agency, Independent Administrative Agency.

The flux density (neutrons/cm$^2$/s) of the neutrons is preferably $10^3$ or higher, and more preferably $10^4$ or higher, because then a neutron scattering profile with a high S/N ratio can be obtained as is the case with the SAXS measurement. The upper limit of the neutron flux density is not particularly limited, and the neutron flux density used is preferably low enough not to cause radiation damage.

In X-ray and neutron scattering measurements, the influence of non-coherent components increases as the scattering angle increases, thereby decreasing the accuracy of the measurement data. Thus, the measurement is preferably performed using the X-rays or neutrons under conditions where q defined by the following Formula I is in the range of not more than 10 Å$^{-1}$, more preferably not more than 1.0 Å$^{-1}$, and still more preferably not more than 0.1 Å$^{-1}$.

$$q = \frac{4\pi \sin(\theta/2)}{\lambda} \quad \text{Formula 1-1}$$

wherein θ is a scattering angle; and λ is a wavelength of X-rays or neutrons.

The X-rays scattered in the SAXS measurement are detected by an X-ray detector, and an image is then generated by an image processor or the like using the X-ray detection data from the X-ray detector.

Examples of the X-ray detectors include two-dimensional detectors (e.g. X-ray films, nuclear emulsion plates, X-ray image pickup tubes, X-ray fluorescent amplifiers, X-ray image intensifiers, X-ray imaging plates, X-ray CCDs, and X-ray amorphous materials), and line sensor one-dimensional detectors. The X-ray detector may be appropriately selected according to the type and the conditions of a material to be analyzed, and the like.

The image processor may appropriately be an ordinary one that can generate X-ray scattering images based on X-ray detection data from an X-ray detector.

The SANS measurement can also be performed based on the same principle as in the SAXS measurement; the neutrons scattered are detected by a neutron detector, and an image is then generated by an image processor or the like using the neutron detection data from the neutron detector. Here, as described above, the neutron detector may be a known two-dimensional detector or one-dimensional detector, and the image processor may be a known one that can generate neutron scattering images. These devices may be appropriately selected.

The material in the present invention is not particularly limited and may be any material such as a polymer material. For example, one or two or more diene polymers may be suitably used. Examples of the diene polymers include rubber materials obtained from one or more conjugated diene compounds, and composite materials formed by combining any of the rubber materials with one or more resins. The conjugated diene compound is not particularly limited, and may be a known compound such as isoprene and butadiene.

Examples of such rubber materials include polymers containing a double bond, including natural rubber (NR), isoprene rubber (IR), butadiene rubber (BR), styrene-butadiene rubber (SBR), acrylonitrile-butadiene rubber (NBR), chloroprene rubber (CR), butyl rubber (IIR), halogenated butyl rubber (X-IIR), and styrene-isoprene-butadiene rubber (SIBR). The polymer material such as a rubber material or a composite material may have one or more modifying groups such as a hydroxy group and an amino group.

The resin is not particularly limited, and examples thereof include those generally used in the rubber industry, including petroleum resins such as C5 aliphatic petroleum resins and cyclopentadiene petroleum resins.

The material may suitably be, for example, a rubber material or composite material, which contains at least one metal-coordinating functional group in its molecular structure. Here, the metal-coordinating functional group may be any one capable of coordinating to a metal and examples thereof include functional groups containing a metal-coordinating atom such as oxygen, nitrogen, or sulfur. Specific examples include a dithiocarbamate group, a phosphate group, a carboxylate group, a carbamate group, a dithioate group, an aminophosphate group, and a thiol group. The material may contain only one or two or more types of functional groups mentioned above.

Examples of metals that can coordinate to the functional group(s) include Fe, Cu, Ag, Co, Mn, Ni, Ti, V, Zn, Mo, W, Os, Mg, Ca, Sr, Ba, Al, and Si. For example, in the case of a polymer material that includes a compound containing such a metal atom ($M_1$) and also contains a metal-coordinating functional group (e.g. —COO), each —COO$M_1$ group binds to one another via coordinate bonds, resulting in overlapping of many —COO$M_1$ groups and thereby forming clusters of aggregated metal atoms. The amount of the metal atom ($M_1$) is preferably 0.01 to 200 parts by mass per 100 parts by mass of the polymer component of the polymer material.

The material may suitably be a filler-containing rubber material or composite material, for instance. Examples of the fillers include carbon black and silica; and $mM_2 \cdot xSiO_y \cdot zH_2O$ wherein $M_2$ represents at least one metal selected from the group consisting of aluminum, calcium, magnesium, titanium, and zirconium, or an oxide, hydroxide, hydrate or carbonate of the metal; m represents a number of 1 to 5; x represents a number of 0 to 10; y represents a number of 2 to 5; and z represents a number of 0 to 10.

Specific examples of the filler represented by $mM_2 \cdot xSiO_y \cdot zH_2O$ include aluminum hydroxide ($Al(OH)_3$), alumina ($Al_2O_3$, $Al_2O_3 \cdot 3H_2O$ (hydrate)), clay ($Al_2O_3 \cdot 2SiO_2$), kaolin ($Al_2O_3 \cdot 2SiO_2 \cdot 2H_2O$), pyrophyllite ($Al_2O_3 \cdot 4SiO_2 \cdot H_2O$), bentonite ($Al_2O_3 \cdot 4SiO_2 \cdot 2H_2O$), aluminum silicate (e.g. $Al_2SiO_5/Al_4(SiO_2)_3 \cdot 5H_2O$), aluminum calcium silicate ($Al_2O_3 \cdot CaO \cdot 2SiO_2$), calcium hydroxide ($Ca(OH)_2$), calcium oxide (CaO), calcium silicate ($Ca_2SiO_4$), magnesium calcium silicate ($CaMgSiO_4$), magnesium hydroxide ($Mg(OH)_2$), magnesium oxide (MgO), talc ($MgO \cdot 4SiO_2 \cdot H_2O$), attapulgite ($5MgO \cdot 8SiO_2 \cdot 9H_2O$), aluminum magnesium oxide ($MgO \cdot Al_2O_3$), titanium white ($TiO_2$), and titanium black ($Ti_nO_{2n-1}$). In a polymer material containing such a filler, the filler particles aggregate to form a cluster. The amount of the filler is preferably 10 to 200 parts by mass per 100 parts by mass of the polymer component of the polymer material.

The rubber material or composite material may contain any of other compounding agents generally used in the rubber industry, such as silane coupling agents, zinc oxide, stearic acid, various antioxidants, oils, waxes, vulcanizing agents, vulcanization accelerators, cross-linkers, and the like. Such a rubber material or composite material may be prepared by a known kneading technique. Examples of such rubber materials and composite materials include those used as rubber materials for tires.

The following will specifically describe the analysis method of determining the neutron scattering length density of a material based on a scattering intensity curve obtained by neutron scattering measurement, with use of a scattering intensity curve obtained by X-ray scattering measurement. For example, in the case of performing small-angle X-ray scattering measurement (SAXS measurement) and contrast variation small-angle neutron scattering measurement (CV-SANS measurement) on a material containing different components, the neutron scattering length density of scatterers in the material may be determined by analyzing scattering intensity curves obtained by these measurements by the following procedure.

Figure 2:
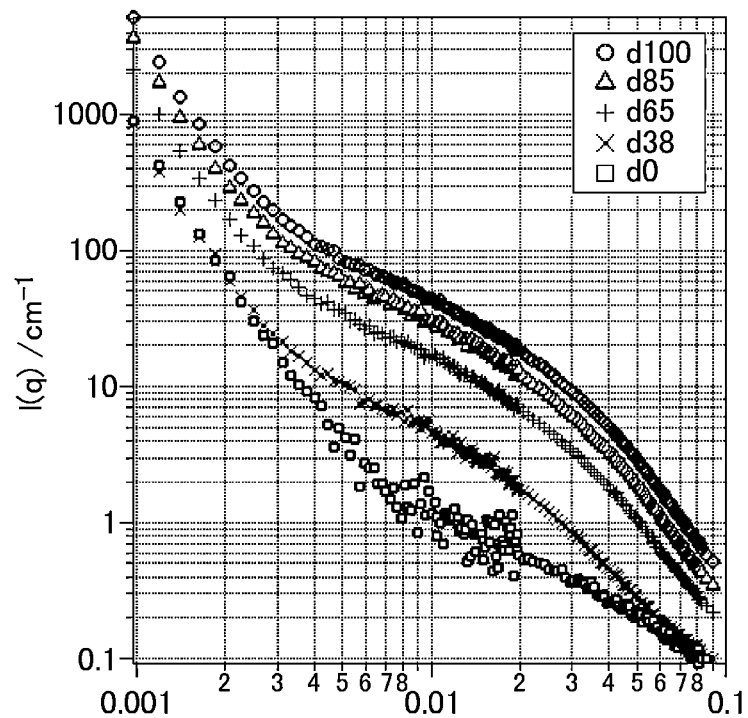
FIG. 2 shows examples of scattering intensity curves of an EXAMPLE sample at the respective concentrations obtained by contrast variation small-angle neutron scattering measurement.

First, X-ray scattering measurement (e.g. small-angle X-ray scattering measurement) is performed on the material to obtain a scattering intensity curve of scatterers in the material (FIG. 1). Separately, contrast variation small-angle neutron scattering measurement, for example, is performed on the material to obtain scattering intensity curves measured at different concentrations (FIG. 2).

Figure 3:
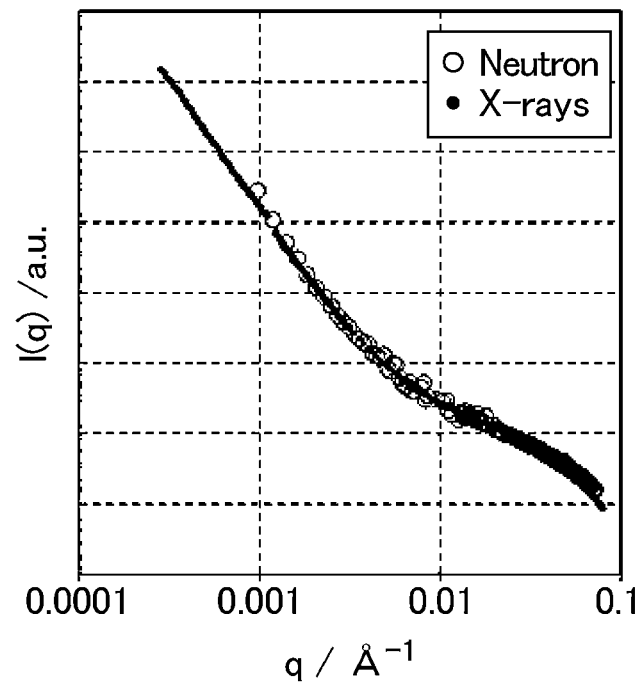
FIG. 3 shows an exemplary figure in which the shape of an X-ray scattering intensity curve obtained by X-ray scattering measurement matches the shape of a scattering intensity curve of only the scatterers detected in the X-ray scattering measurement, separated from scattering intensity curves obtained by neutron scattering measurement.

Then, based on the scattering intensity curves with different concentrations obtained by contrast variation small-angle neutron scattering measurement, the neutron scattering length density of scatterers is varied such that the shape of the X-ray scattering intensity curve obtained by X-ray scattering measurement matches the shape of a scattering intensity curve of only the scatterers detected by the X-ray scattering measurement, separated from the scattering intensity curves obtained by the neutron scattering measurement according to the method disclosed in JP 2013-30286 A (which is incorporated by reference in its entirety) (FIG. 3). Then the scattering length density thus determined can be regarded as an accurate value of the neutron scattering length density.

The following will specifically describe the procedure of accurately determining the neutron scattering length density by matching the shape of the X-ray scattering intensity curve obtained by X-ray scattering measurement to the shape of the scattering intensity curve of only the scatterers detected by the X-ray scattering measurement, separated from the scattering intensity curves with different concentrations obtained by contrast variation small-angle neutron scattering measurement.

As mentioned above, contrast variation small-angle neutron scattering measurement is performed. This is a technique in which, for example, structural analysis of multiple substances contained in a sample is performed based on small-angle neutron scattering of multiple samples subjected to contrast variation (CV). The contrast variation herein means varying the deuteration level of a swelling solvent or a target material to vary the scattering length density thereof and thus vary the scattering length density difference (contrast) from the scattering length density of each of multiple substances (e.g. rubber, filler) contained in the material.

For example, the contrast variation small-angle neutron scattering may be performed on multiple samples prepared using mixed solvents of deuterated toluene and toluene at different (deuterated toluene/toluene) ratios as swelling solvents. More specifically, five samples prepared using a swelling solvent with a deuterated toluene percentage by mass of 0%, 38%, 65%, 85%, and 100%, respectively, may be measured. Hereinafter, a sample with a deuterated toluene percentage (by mass) in a swelling solvent of 0% is also referred to as "d0", 38% as "d38", 65% as "d65", 85% as "d85", and 100% as "d100".

FIG. 2 shows the scattering intensity curves of the five samples (d0, d38, d65, d85, and d100).

The scattering intensity I(q) of a sample can be expressed as the sum of partial scattering functions of components contained in the sample. Thus, from the scattering intensities I(q) of the five samples, the following functions are calculated: the scattering function $S_{cc}(q)$ of scatterers including zinc acrylate in the sample, the partial scattering function $S_{pp}(q)$ of scatterers including rubber in the sample, and the partial scattering function $S_{cp}(q)$ indicating the interaction between the scatterers including zinc acrylate and the rubber. The scattering intensity I(q) of the sample is represented by the following Formula (I):

$$I(q)=(\rho_c-\rho_w)^2 S_{cc}(q)+(\rho_p-\rho_w)^2 S_{pp}(q)+2(\rho_c-\rho_w)(\rho_p-\rho_w)S_{cp}(q) \quad (I)$$

wherein $\rho_c$ represents the scattering length density of scatterers including zinc acrylate; $\rho_w$ represents the scattering length density of a swelling solvent; $\rho_p$ represents the scattering length density of rubber; $(\rho_c-\rho_w)$ represents the scattering length density difference between the scatterers including zinc acrylate and the swelling solvent; and $(\rho_p-\rho_w)$ represents the scattering length density difference between the rubber and the swelling solvent.

Using Formula (II) with the scattering intensities $I_n(q)$ of the five samples (n=1 to 5), the scattering length density difference $\Delta\rho_c$ between scatterers including zinc acrylate and a swelling solvent in each sample, and the scattering length density difference $\Delta\rho_p$ between rubber and a swelling solvent in each sample, the following functions can be calculated: the partial scattering function $S_{cc}(q)$ of the scatterers including zinc acrylate, the partial scattering function $S_{pp}(q)$ of the scatterers including rubber, and the partial scattering function $S_{cp}(q)$ indicating the interaction between the scatterers including zinc acrylate and the rubber. Formula (II) is a matrix equation corresponding to Formula (I) for the five samples. The singular value decomposition thereof allows the determination of $S_{cc}(q)$, $S_{cp}(q)$, and $S_{pp}(q)$.

$$\begin{pmatrix} I_1(q) \\ \vdots \\ I_n(q) \end{pmatrix} = \begin{pmatrix} \Delta_1\rho_c^2 & 2\Delta_1\rho_c\cdot\Delta_1\rho_p & \Delta_1\rho_p^2 \\ \vdots & \vdots & \vdots \\ \Delta_n\rho_c^2 & 2\Delta_n\rho_c\cdot\Delta_n\rho_p & \Delta_n\rho_p^2 \end{pmatrix} \cdot \begin{pmatrix} S_{cc}(q) \\ S_{cp}(q) \\ S_{pp}(q) \end{pmatrix} \quad (II)$$

The dots in FIG. 3 indicate the partial scattering function $S_{cc}(q)$ of the scatterers including zinc acrylate calculated from the Formula (II). As shown in FIG. 3, the neutron scattering length density can be accurately determined by calculation such that the shape of the scattering intensity curve of the scatterers in a material obtained by small-angle X-ray scattering measurement matches the shape of the scattering intensity curve of only the scatterers detected by the small-angle X-ray scattering measurement, separated from the scattering intensity curves obtained by contrast variation small-angle neutron scattering measurement.

EXAMPLES

The present invention will be described in greater detail with reference to, but not limited to, examples.

The chemicals used in the examples and comparative examples are listed below.

(Reagents)
BR730: butadiene rubber (JSR Corp.)
SANCELER SR: product of SANSHIN CHEMICAL INDUSTRY CO., LTD.
PERCUMYL D: product of Ouchi Shinko Chemical Industrial Co., Ltd.

(Preparation of Samples)

According to each of the compositions shown in Table 1, the materials were kneaded using a Banbury mixer and a roll kneader. The kneaded materials were press-molded at 170° C. for 20 minutes or at 200° C. for five minutes, thereby providing an about 1-mm-thick sample sheet (sample 1: press-molded at 170° C. for 20 minutes; sample 2: press-molded at 200° C. for five minutes).

The samples 1 and 2 were subjected to the following SAXS measurement and CV-SANS measurement, thereby providing SAXS scattering intensity curves and CV-SANS scattering intensity curves. In addition, the samples were observed by TEM.

1. SAXS Measurement

An about 1-mm-thick sample sheet that had been swollen in toluene for 12 hours was mounted on a sample holder, and the sample was irradiated with X-rays at room temperature. A scattering intensity curve obtained by the BL03XU measurements and a scattering intensity curve obtained by the BL20XU measurements were combined by least squares. The two curves were combined such that the scattering intensity curve obtained by the BL03XU measurements at wider angles was fixed, and the scattering intensity curve obtained by the BL20XU measurements at smaller angles was then shifted. Thus, a scattering intensity curve $I_{(q)}$ of each sample was obtained by SAXS measurement. The scattering intensity curve $I_{(q)}$ thus obtained is derived from the scatterers including zinc acrylate contained in SANCELER SR.

(SAXS Apparatus)
SAXS: SAXS measurement apparatus provided with the beamlines BL03XU and BL20XU of the large synchrotron radiation facility "SPring-8" belonging to Japan Synchrotron Radiation Research Institute (Measurement Conditions)
Brilliance of X-rays: $5\times10^{12}$ photons/s/mrad$^2$/mm$^2$/0.1% bw
Number of photons in X-rays: $2\times10^9$ photons/s
Energy of X-rays: 8 keV (BL03XU), 23 keV (BL20XU)
Distance between sample and detector: 3 m (BL03XU), 160 m (BL20XU)

(Detector)
Two-dimensional detector (image intensifier and CCD camera)

2. CV-SANS Measurement

Five swelling solvents were prepared with a ratio (by mass) between deuterated toluene and toluene of 100:0, 85:15, 65:35, 38:62, and 0:100, respectively. Then, about 1-mm-thick sample sheets that had been previously swollen for 12 hours in the respective swelling solvents were prepared. Subsequently, each of these sample sheets swollen to equilibrium was mounted on a sample holder, and then irradiated with neutrons at room temperature. Absolute scattering intensity curves obtained by measuring the sample at distances of 2.5 m and 10 m from the detector and with a focusing lens were combined by least squares. These three curves were combined such that the scattering intensity curve obtained by measuring the sample at a distance of 2.5 m from the detector was fixed, and the scattering intensity curves obtained by measuring the sample at a distance of 10 m and with a focusing lens were then shifted. Thus, scattering intensity curves $I_{(q)}$ of each sample were obtained by CV-SANS measurement.

(SANS Apparatus)
  SANS: SANS measurement apparatus provided with the SANS-J beamline at the JRR-3 research reactor belonging to Japan Atomic Energy Agency, Independent Administrative Agency
(Measurement Conditions)
  Wavelength of neutrons: 6.5 Å
  Flux density of neutrons: $9.9 \times 10^7$ neutrons/cm$^2$/s
  Distance between sample and detector: 2.5 m and 10 m (in order to obtain the information at smaller angles, the sample was also measured at a distance of 10 m from the detector, using a focusing lens.)
(Detector)
  Two-dimensional detector ($^3$He two-dimensional detector and two-dimensional photomultiplier+ZnS/$^6$LiF detector)
3. TEM Observation
  The samples were observed using the transmission electron microscope (TEM) JEM-2100F (JEOL Ltd.) at an accelerating voltage of 200 kV.

Example 1

For the sample 1, the neutron scattering length density of the scatterers including zinc acrylate was varied such that the scattering intensity curve $I_{(q)}$ obtained by SAXS measurement matched a scattering intensity curve of the scatterers including zinc acrylate, separated from the scattering intensity curves $I_{(q)}$ obtained by CV-SANS measurement according to the method described in JP 2013-30286 A. This resulted in a value (of neutron scattering length density) of $1.00 \times 10^{-6}$ Å$^{-2}$.

Example 2

The same procedure was performed as in Example 1, except that the sample 2 was used instead of the sample 1, resulting in a value (of neutron scattering length density) of $1.40 \times 10^{-6}$ Å$^{-2}$.

Comparative Example 1

The neutron scattering length density of poly zinc acrylate (=$2.15 \times 10^{-6}$ Å$^{-2}$) was used as the neutron scattering length density of the sample 1.

Comparative Example 2

The neutron scattering length density of poly zinc acrylate (=$2.15 \times 10^{-6}$ Å$^{-2}$) was used as the neutron scattering length density of the sample 2.

TABLE 1

| | | Example | | Comparative Example | |
|---|---|---|---|---|---|
| | | (1) | (2) | (1) | (2) |
| Composition | BR730 (phr) | 100 | 100 | 100 | 100 |
| | SANCELER SR (phr) | 30 | 30 | 30 | 30 |
| | PERCUMYL D (phr) | 1 | 1 | 1 | 1 |
| | Molding temperature (° C.) | 170 | 200 | 170 | 200 |
| Neutron scattering length density ($10^{-6}$ Å$^{-2}$) | | 1.00 | 1.40 | 2.15 | 2.15 |

Table 1 shows that Comparative Examples 1 and 2 provided no difference in neutron scattering length density between the sample 1 and the sample 2, whereas Examples 1 and 2 employing the evaluation method of the present invention provided a difference in neutron scattering length density between the samples. This means that the present invention enables accurate determination of the neutron scattering length density.

Figure 4:
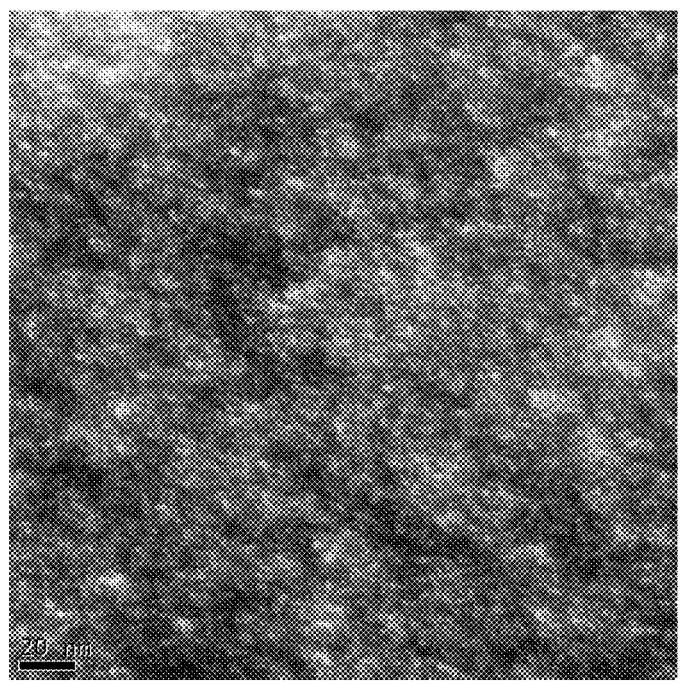
FIG. 4 is an example of an electron microscopic picture of the sample 1 in TEM observation.
Figure 5:
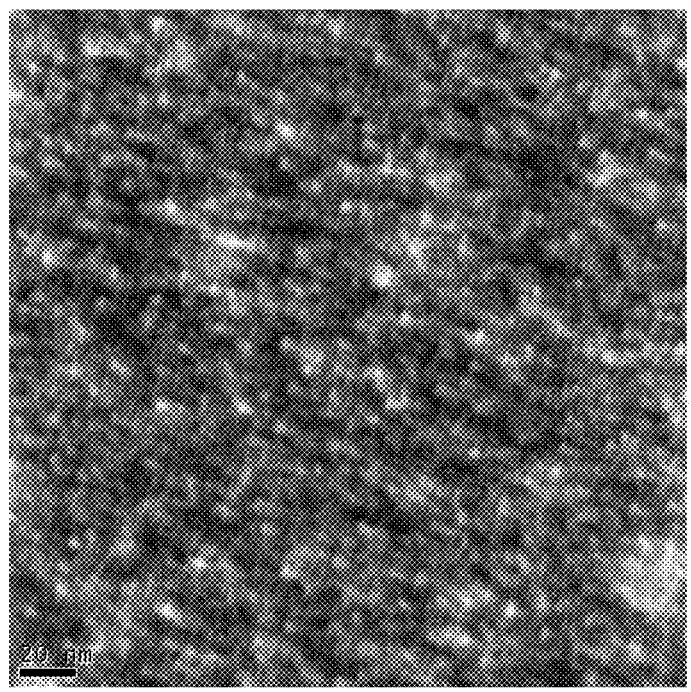
FIG. 5 is an example of an electron microscopic picture of the sample 2 in TEM observation.

In addition, the TEM observation shows a difference in the density of nanoclusters of zinc acrylate between the sample 1 (FIG. 4) and the sample 2 (FIG. 5), with the sample 2 having a higher density (brighter result). However, since the transmission measurement gives results in which information is accumulated in the film thickness direction, it did not allow quantitative analysis of the density of nanoclusters of zinc acrylate with high accuracy. In contrast, it was demonstrated that the evaluation method of the present invention detected a difference in neutron scattering length density between the samples 1 and 2 of Examples 1 and 2. This means that the present invention enables quantitative analysis of the density of nanoclusters of zinc acrylate with high accuracy.

The invention claimed is:

1. A method of evaluating a neutron scattering length density of scatterers in a material, the material being a mixture of multiple compositions, the method comprising the steps of:
  performing an X-ray scattering measurement on the material;
  obtaining an X-ray scattering intensity curve of scatterers in the material;
  performing a contrast variation neutron scattering measurement, separately from the X-ray scattering measurement, on the material;
  obtaining scattering intensity curves corresponding to different concentrations;
  determining the neutron scattering length density by varying the neutron scattering length density of scatterers in the material based on the scattering intensity curves corresponding to different concentrations, such that a shape of the X-ray scattering intensity curve matches a shape of a scattering intensity curve, out of said scattering intensity curves obtained by the contrast variation neutron scattering measurement, which is obtained by separating the scattering intensity curve of only the scatterers detected by the X-ray scattering measurement from the scattering intensity curves obtained by the contrast variation neutron scattering measurement; and
  determining the molecular structure of scatterers of the material based on the determined neutron scattering length density.

2. The method of evaluating a neutron scattering length density according to claim 1, wherein the X-ray scattering measurement is small-angle X-ray scattering measurement, and the neutron scattering measurement is small-angle neutron scattering measurement.

3. The method of evaluating a neutron scattering length density according to claim 1, wherein the material comprises one or more diene polymers.

4. The method of evaluating a neutron scattering length density according to claim 1, further comprising the step of determining the mixing ratio of the material from the neutron scattering length density.

* * * * *